United States Patent
Klostermann et al.

(10) Patent No.: US 9,725,538 B2
(45) Date of Patent: Aug. 8, 2017

(54) SILICONE (METH)ACRYLATE PARTICLES, PROCESSES FOR THEIR PREPARATION AND USE THEREOF

(71) Applicant: Evonik Industries AG, Essen (DE)

(72) Inventors: Michael Klostermann, Essen (DE);
Susann Wiechers, Essen (DE);
Matthias Naumann, Hamburg (DE);
Joachim Venzmer, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 59 days.

(21) Appl. No.: 14/572,212

(22) Filed: Dec. 16, 2014

(65) Prior Publication Data
US 2015/0175724 A1  Jun. 25, 2015

(30) Foreign Application Priority Data
Dec. 19, 2013 (DE) .......... 10 2013 226 568

(51) Int. Cl.
| | |
|---|---|
| *C08F 120/10* | (2006.01) |
| *A61Q 19/00* | (2006.01) |
| *A61K 8/42* | (2006.01) |
| *A61K 8/891* | (2006.01) |
| *A61K 8/02* | (2006.01) |
| *C08K 3/36* | (2006.01) |
| *C08K 5/14* | (2006.01) |
| *C08G 77/20* | (2006.01) |

(52) U.S. Cl.
CPC .......... *C08F 120/10* (2013.01); *A61K 8/0241* (2013.01); *A61K 8/42* (2013.01); *A61K 8/891* (2013.01); *A61Q 19/00* (2013.01); *C08K 3/36* (2013.01); *C08K 5/14* (2013.01); *A61K 2800/10* (2013.01); *A61K 2800/412* (2013.01); *A61K 2800/622* (2013.01); *A61K 2800/654* (2013.01); *A61K 2800/80* (2013.01); *C08G 77/20* (2013.01); *Y10T 428/2982* (2015.01); *Y10T 428/2998* (2015.01)

(58) Field of Classification Search
CPC ... B01J 13/14; B01J 13/18; B01J 13/02; B01J 13/043; A61K 19/00; A61K 8/42; A61K 8/0241; A61K 5/14; A61K 2800/80; A61K 2800/10; A61K 2800/412; A61K 2800/622; A61K 2800/654
See application file for complete search history.

(56) References Cited

U.S. PATENT DOCUMENTS

| | | | |
|---|---|---|---|
| 3,615,972 A | 10/1971 | Morehouse, Jr. et al. | |
| 4,761,454 A | 8/1988 | Oba et al. | |
| 5,384,479 A | 1/1995 | Taniguchi | |
| 5,462,884 A | 10/1995 | Taniguchi | |
| 5,854,369 A | 12/1998 | Geck et al. | |
| 6,207,782 B1 | 3/2001 | Czech et al. | |
| 6,552,091 B1 | 4/2003 | Boinowitz et al. | |
| 6,753,399 B2 | 6/2004 | Inokuchi | |
| 7,094,462 B1* | 8/2006 | Yokoyama et al. | A61K 8/0208 428/304.4 |
| 7,727,599 B2 | 6/2010 | Doehler et al. | |
| 7,759,402 B2 | 7/2010 | Venzmer et al. | |
| 8,247,525 B2 | 8/2012 | Schubert et al. | |
| 8,268,939 B2 | 9/2012 | Ebbrecht et al. | |
| 8,344,033 B2 | 1/2013 | Gottschalk-Gaudig et al. | |
| 8,466,248 B2 | 6/2013 | Meyer et al. | |
| 8,486,677 B2 | 7/2013 | Thum et al. | |
| 8,497,234 B2 | 7/2013 | Mayer et al. | |
| 8,653,214 B2 | 2/2014 | Venzmer et al. | |
| 8,772,423 B2 | 7/2014 | De Gans et al. | |
| 8,796,000 B2 | 8/2014 | Thum et al. | |
| 2001/0031792 A1 | 10/2001 | Silber et al. | |
| 2004/0029978 A1 | 2/2004 | Chane-Ching | |
| 2004/0063818 A1 | 4/2004 | Silber et al. | |
| 2004/0156808 A1 | 8/2004 | Kazuhiko et al. | |
| 2007/0197678 A1 | 8/2007 | Cavaleiro et al. | |
| 2007/0208109 A1 | 9/2007 | Kautz et al. | |
| 2007/0281878 A1 | 12/2007 | Gottschalk-Gaudig et al. | |
| 2008/0004357 A1 | 1/2008 | Meyer et al. | |
| 2009/0007483 A1 | 1/2009 | Hansel et al. | |
| 2009/0104238 A1 | 4/2009 | Stark et al. | |
| 2009/0149573 A1* | 6/2009 | Venzmer et al. | C08F 283/12 523/201 |
| 2010/0041629 A1 | 2/2010 | Giessler-Blank et al. | |
| 2010/0071849 A1 | 3/2010 | Knott et al. | |
| 2012/0068110 A1 | 3/2012 | Schubert et al. | |
| 2013/0213267 A1 | 8/2013 | Fiedel et al. | |
| 2013/0217930 A1 | 8/2013 | Haensel et al. | |
| 2013/0310530 A1* | 11/2013 | Jha et al. | A61K 8/0208 526/279 |
| 2014/0134125 A1 | 5/2014 | Dahl et al. | |

FOREIGN PATENT DOCUMENTS

| | | |
|---|---|---|
| DE | 10011564 C1 | 9/2001 |
| DE | 102004014704 | 10/2005 |

(Continued)

OTHER PUBLICATIONS

Binks, B.P., et al., "Particles as surfactants—similarities and differences", Current opinion in colloid & interface science, 7, Mar. 2002, pp. 21-41.

(Continued)

*Primary Examiner* — Nathan M Nutter
(74) *Attorney, Agent, or Firm* — Scully, Scott, Murphy & Presser, P.C.

(57) ABSTRACT

Particles obtainable by polymerization of a siloxane which has at least one (meth)acrylate group of the formula (I)

$$-O-C(O)-CR=CH_2 \qquad (I)$$

where R=—H or —$CH_3$, which are characterized in that the siloxane has an average molar ratio of groups of the formula (I) to Si atoms of less than 0.1 are provided.

12 Claims, No Drawings

(56) References Cited

FOREIGN PATENT DOCUMENTS

| | | |
|---|---|---|
| DE | 102004053314 A1 | 5/2006 |
| DE | 102007058713 A1 | 6/2009 |
| EP | 0744432 A1 | 11/1996 |
| EP | 0765656 A1 | 4/1997 |
| EP | 0765896 A1 | 4/1997 |
| EP | 0834305 A2 | 4/1998 |
| EP | 1074575 A2 | 2/2001 |
| EP | 1130046 A2 | 9/2001 |
| EP | 2273966 | 1/2011 |
| FR | 2682534 | 4/1993 |
| FR | 2808704 | 11/2001 |
| JP | 200063462 | 2/2000 |
| JP | 20032973 | 1/2003 |
| JP | 2003301047 | 10/2003 |
| JP | 200670378 | 3/2006 |
| WO | WO0031203 | 6/2000 |
| WO | WO2006016968 | 2/2006 |
| WO | WO2007115872 | 10/2007 |
| WO | WO2012100884 A1 | 8/2012 |

OTHER PUBLICATIONS

Landfester, K., et al., "Polydimethyl siloxane latexes and copolymers by polymerization and polyaddition in miniemulsion" 46, 2005, pp. 9892-9898.

Pickering, S.U., "Emulsions", Journal of the Chemical Society, Transactions, Jan. 1907, 91, pp. 2001-2021.

Hassander, H., et al, "The mechanism of emulsion stabilization by small silica (LUDOX) particles", 40, Feb. 1989, pp. 93-105.

Cauvin, S., et al., "Pickering stabilized miniemulsion polymerization: Preparation of clay armored latexes", Macromolecules, Aug. 2005, 38, pp. 7887-7889.

Binks, B.P., et al., "Direct Measurement of Contact Angles of Silica Particles in Relation to Double Inversion of Pickering Emulsions" Langmuir, Apr. 2013, 29, pp. 4923-4927.

European Search Report dated Apr. 28, 2015, received in a corresponding foreign application.

Schrader, K. et al., "Grundlagen and Rezepturen der Kosmetika" ["Principles and Formulations of Cosmetics"], 1989, 2nd edition, p. 329 to 341, Hüthig Buch Verlag Heidelberg.

* cited by examiner

SILICONE (METH)ACRYLATE PARTICLES, PROCESSES FOR THEIR PREPARATION AND USE THEREOF

FIELD OF THE INVENTION

The present invention relates to particles obtainable by polymerization of a siloxane which has at least one (meth)acrylate group of formula (I)

where R=—H or —CH$_3$, which are characterized in that the siloxane has an average molar ratio of groups of the formula (I) to Si atoms of less than 0.1, to a process comprising the steps: a) producing an emulsion from an aqueous phase and an organic phase, where the organic phase has at least one siloxane which has at least one (meth)acrylate group of formula (I), with the addition of at least one emulsifier, preferably a solid-body emulsifier and mixing the two phases, where the organic phase forms the inner phase of the emulsion, and b) fully polymerizing the inner phase in the presence of a radical initiator which is more soluble in the organic phase than in the aqueous phase, which is characterized in that the siloxane used has an average molar ratio of groups of formula (I) to Si atoms of less than 0.1, to particles produced accordingly, and to the use of the particles, preferably in cosmetic formulations.

BACKGROUND

It is known to use hydrophobic or hydrophobicized particles or silicone resin particles in cosmetic formulations, e.g., as a matting agent, as absorbers for skin sebums or for producing a silky skin feel. Moreover, corresponding particles are often used in make-up formulations in order to improve the holding power of the make-up on the skin. Silicone-rubber powders or powders of silicone elastomers are often used for this purpose.

Several methods are known for producing corresponding particles. In principle, irregularly shaped silicone elastomer particles can be obtained by grinding processes of the respective bulk elastomers, but spheroidal or spherical particles generally offer application-related advantages, particularly if pleasant tactile properties of particle-additivated materials and formulations are desired. Usually, such particles are produced by crosslinking reactions within starting material droplets or growing on/application of a polymer to a particle core. Crosslinking reactions can be, e.g., hydrosilylation reactions, condensation reactions, dehydrogenative coupling reactions or free-radical polymerization.

Silicone particles of hydrosilylations are described, for example in U.S. Pat. No. 4,761,454, JP 2003301047 and EP 1 074 575, hydrolysis and condensation reactions for producing silicone particles can be found in EP 1 130 046, WO 2006/016968, JP 2003002973, U.S. Pat. No. 6,753,399, EP 0 765 896 and EP 0 744 432, while U.S. Patent Publication No. 2004/0156808 describes a dehydrogenative coupling reaction for this purpose. Finally, DE 10 2004 053 314 describes copolymers of at least two different macromonomers obtainable by free-radical polymerizations.

The production of free-radically crosslinked silicone acrylate particles was reported for the first time in 2005 in "Polydimethyl siloxane latexes and copolymers by polymerization and polyaddition in miniemulsion" (Katharina Landfester, Ute Pawelzik, Markus Antonietti, Polymer, 46 (2005), 9892-9898). In the aforementioned publication, the miniemulsion polymerization of silicone acrylates to nanoscale particles using a conventional emulsifier and a customary molecular radical initiator, such as, for example, AIBN, is described in detail. However, the described process does not produce microscale particles which have the desired application-related properties, i.e., good skin feel desired for personal care applications cannot be obtained with such particles.

Solid-body-stabilized, aqueous emulsions were described in 1907 by S.U. Pickering ("Emulsions", Spencer Umfreville Pickering, Journal of the Chemical Society, Transactions (1907), 91, 2001 2021) and are considered to be particularly stable to coalescence. Thus, DE 10 2004 014 704 describes the preparation of emulsions which are stabilized with pyrogenically produced particles. A good overview of the properties of such stabilizing solids particles can be found in "Particles as surfactants—similarities and differences" by Bernard P. Binks (Current opinion in colloid & interface science, 7 (2002), 21-41). The prior art also includes so-called "Janus particles", amphiphilic particles with a hemispherically modified surface, as described e.g. in FR 2 808 704. Of particularly good suitability for emulsion stabilization are nanoscale, predominantly inorganic particles, e.g., silica particles which are commercially available as "LUDOX®" in the form of aqueous sols or dispersions from Grace Davison. U.S. Pat. No. 3,615,972 (1967) describes for the first time the use of LUDOX® particles for the emulsion stabilization of methyl methacrylate with subsequent polymerization. The mechanism of the stabilizing effect discussed in the literature is the agglomeration of the particles and the accumulation of the agglomerates at the water/oil interface ("The mechanism of emulsion stabilization by small silica (LUDOX®) particles", Helen Hassander, Beatrice Johansson, Bertil Törnell, Colloids and Surfaces, 40, (1989), 93-105).

The suspension polymerization of Pickering emulsions of insoluble or poorly soluble starting materials is usually started by means of a radical initiator dissolved in the oil phase. The use of water-soluble radical initiators with styrene as the sole monomer leads to incomplete conversion and coagulation ("Pickering stabilized miniemulsion polymerization: Preparation of clay armoured latexes", Séverine Cauvin, Patrick J. Colver, and Stefan A. F. Bon, Macromolecules 2005, 38, 7887-7889).

DE 102007058713 describes a process for the preparation of microscale silicone (meth)acrylate particles by suspension polymerization using a solid-body emulsifier and a water-soluble redox radical initiator.

JP 2006-070378 describes a process for preparing dispersions comprising silicone (meth)acrylate particles. The preparation takes place using an emulsifier and a water-soluble initiator. JP 2000-063462 describes the preparation of hydrophilic siloxane latex emulsions.

One disadvantage of this process is that high concentrations of a water-soluble radical initiator are necessary in order to ensure adequate crosslinking of the particles. Moreover, these high radical initiator concentrations require the use of large amounts of a potassium phosphate buffer in order to keep the pH of the system constant during the polymerization. As a result, this process results in an ecologically undesired high salt burden of the wastewater resulting from the process. Moreover, complex, cost-intensive washing cycles are required in order to remove residues of radical initiator and buffer from the product after the polymerization.

A further disadvantage of the silicone (meth)acrylate particles produced in this way is that the polymerized particles have a relatively high content of (meth)acrylate groups that have not fully reacted, but are bonded covalently to the polymer. These often lead to an unpleasant odor being perceptible in the presence of ester-cleaving or transesterifying substances, such as for example, water or alcohols, and this odor makes the particles unusable for various applications, especially those which come into contact with the consumer.

Moreover, the particles prepared in this way have the disadvantage that they mostly have a yellowish-brownish discoloration as a result of the action of the redox radical initiator, which is undesired particularly for applications in the cosmetic sector. As a result, the preparation of the particles often requires an additional bleaching step, for example with $H_2O_2$, which is unfavourable both from an ecological and economical point of view.

A further disadvantage of the particles prepared according to DE 102007058713 is that they have irregular, nonspherical structures, which has an adverse effect on the skin feel of the particles.

Besides the preparation, the use of a very wide variety of silicone-based particles in cosmetic compositions is also described in a number of publications.

Thus, for example, EP 0834305 describes gel-like cosmetic skin-treatment compositions which comprise spherical powders of organopolysiloxanes with an average particle size from 1 to 15 μm. The particles added are in particular hydrophobicized and/or silicone-treated inorganic powders.

EP 0765656 describes cosmetic water-in-oil emulsions as cosmetic compositions which comprise powders of spherical, elastomeric organopolysiloxane particles. Besides the elastomeric (mouldable) particles, these compositions have hydrophobicized silica particles.

FR 2682534 describes skin cosmetics which have two different particle fractions, where the one fraction consists of non-mouldable particles, preferably glass beads, and the other consists of mouldable, i.e., elastic, particles.

The common feature of the cited documents is that a pleasant (soft), powdery skin feel is to be achieved through the use of the elastomer particles.

The use of non-elastomeric silicone acrylate and methacrylate particles in cosmetic applications was reported for the first time in DE 102007058713 and in WO 2012/100884 A1. The particles described in WO 2012/100884 A1 have a non-optimal skin feel. Moreover, these silicone (meth)acrylate particles in the cosmetic compositions have the above-described disadvantages attributable to their preparation process based on a water-soluble radical initiator; in particular, the particles have dimples (indentations), which has an adverse effect on their skin feel.

SUMMARY OF THE INVENTION

An object of f the present invention was to provide silicone (meth)acrylate particles which do not have one or more disadvantages of the particles of the prior art and are characterized by a particularly advantageous skin feel.

Surprisingly, it has been found that the object is achieved by particles obtainable by polymerization of a siloxane which has at least one (meth)acrylate group, where the siloxane has an average molar ratio of (meth)acrylate groups to Si atoms of less than 0.1. Moreover, it has been found that particles with a particularly advantageous skin feel can be provided if an oil-soluble radical initiator is used for producing the particles since a more uniform shape of the particles is thus produced.

The present invention therefore provides a process comprising the steps: a) producing an emulsion from an aqueous phase and an organic phase, wherein the organic phase has at least one radical initiator and at least one siloxane which has at least one (meth)acrylate group of formula (I)

—O—C(O)—CR=CH$_2$    (I)

where R=—H or —CH$_3$,
with the addition of at least one emulsifier, preferably of a solid-body emulsifier and mixing the two phases, where the organic phase forms the inner phase of the emulsion, and b) fully polymerizing the inner phase in the presence of a radical initiator which is more soluble in the organic phase than in the aqueous phase, which is characterized in that the siloxane used has an average molar ratio of groups of formula (I) to Si atoms of less than 0.1.

The present invention further provides particles which are obtainable by such a process.

The present invention likewise provides particles obtainable by polymerization of a siloxane which has at least one (meth)acrylate group of formula (I)

—O—C(O)—CR=CH$_2$    (I)

where R=—H or —CH$_3$, which are characterized in that the siloxane has an average molar ratio of groups of formula (I) to Si atoms of less than 0.1.

The present invention likewise provides the use of the particles according to the invention alone or in a mixture with further particles, pigments and/or further customary additives in the form of powders or dispersions in cosmetic or pharmaceutical preparations or in care compositions.

Moreover, the present invention provides compositions comprising the particles according to the invention or the particles produced according to the invention.

Compared to the silicone (meth)acrylate particles described in WO 2012/100884 A1, the silicone (meth)acrylate particles according to the invention have the advantage that they are characterized by a particularly silky-velvety skin feel. This may possibly be attributed to the fact that the particles have a more uniform, spherical morphology through the use of an oil-soluble radical initiator, as a result of which they are characterized by improved sensory properties.

It is a further advantage of the silicone (meth)acrylate particles according to the invention that, as a consequence of their preparation process based on an oil-soluble radical initiator, they contain a lower content of (meth)acrylate groups that are not polymerized but are covalently bonded to the polymer, as a result of which the hydrolysis stability of the particles is considerably increased, particularly in the presence of ester-cleaving or transesterifying substances, such as, for example, water or alcohols. This is advantageous for applications in the sectors of cosmetics, food packaging, medicinal products etc. where contact between the particles and water and alcohols under hydrolysis conditions cannot be ruled out. As a result, both the quality and also the safety of corresponding products is increased.

Furthermore, the silicone (meth)acrylate particles of the present invention have the advantage that, as a result of their preparation process, they have no discolorations, meaning that subsequent complex bleaching steps are not necessary. Moreover, by virtue of using an oil-soluble radical initiator during the preparation of the silicone (meth)acrylate particles of the present invention, fewer aqueous waste products are formed. Thus, firstly the salt content present in the aqueous waste waters is lower than would be the case when using water-soluble initiators. This means that during the preparation process of the present invention fewer wash cycles are required for purifying the particles. All of these points produce ecological as well as economical advantages in terms of processing.

DETAILED DESCRIPTION OF THE INVENTION

The particles according to the invention, and their preparation and uses are described below by way of example without any intention of limiting the invention to these exemplary embodiments.

When ranges, general formulae or compound classes are specified hereinafter, these shall include not just the corresponding ranges or groups of compounds that are explicitly mentioned but also all sub-ranges and sub-groups of compounds which can be obtained by removing individual values (ranges) or compounds. Where documents are cited in the context of the present description, it is intended that their content fully form part of the disclosure content of the present invention. Where, in the context of the present invention, compounds, such as e.g., organomodified polysiloxanes, are described which can have different units multiple times, then these can occur in random distribution (random oligomer or polymer) or arranged (block oligomer or block polymer) in these compounds. Percentages are by weight, unless otherwise stated. Average values referred to hereinbelow are number averages, unless otherwise stated. Where material properties are given below, such as e.g., viscosities or the like, then, unless stated otherwise, these are the material properties at 25° C. If parameters are given below which have been determined by measurement, then, unless stated otherwise, the measurements have been carried out at a temperature of 25° C. and a pressure of 101.325 Pa. When chemical (empirical) formulae are used in the present invention, the reported indices can be not only absolute numbers but also average values. Indices relating to polymeric compounds are preferably average values.

The process according to the invention comprises the steps:
  a) Producing an emulsion of an aqueous phase and of an organic phase, wherein the organic phase has at least one radical initiator and a siloxane which has at least one (meth)acrylate group of formula (I)

where R=—H or —CH$_3$, preferably —CH$_3$,
  with the addition of at least one solid-body emulsifier and mixing the two phases, where the organic phase forms the inner phase of the emulsion, and
  b) fully polymerizing the inner phase in the presence of a radical initiator which is more soluble in the organic phase than in the aqueous phase, characterized in that the siloxane has an average molar ratio of groups of formula (I) to Si atoms of less than 0.1, preferably from 0.02 to 0.08.

Preference is given to using a siloxane which satisfies formula (II)

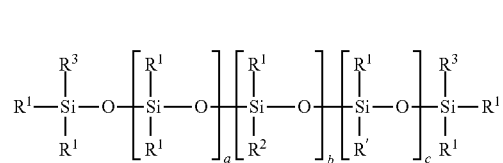

where
R$^1$=identical or different alkyl radicals, preferably methyl radicals,

R$^2$=identical or different radicals not the same as R', R$^1$ and R$^3$ which have carbon atoms, R$^3$=identical or different radicals R$^1$ or radicals which have at least one group according to formula (I), R'=identical or different radicals which have at least one group according to formula (I), a=9 to 250, b=0 to 20, preferably 0 or 1, preferably 0, c=0 to 20, and with the proviso that per siloxane of formula (II), if c=0 at least one radical R$^3$ is present which has at least one group according to formula (I). The numerical values for a, b and c are preferably statistical average values.

Besides carbon atoms, the radicals R$^2$ can also have one or more hydrogen, oxygen and silicone atoms. Preferably, the radicals R$^2$ have no silicon atoms. Preferred radicals R$^2$ are those which have an acetate group. Particularly preferred radicals R$^2$ are those which satisfy the formula —(CH$_2$)$_3$—O—CH$_2$—CH(OH)—CH$_2$—O—C(O)—CH$_3$.

Preferably, at least one siloxane of formula (II) in which variable 'a' assumes a value from 50 to 220, preferably from 75 to 180, is used in the process according to the invention.

The siloxane used in the process according to the invention is preferably a siloxane of formula (II) in which variable 'c' assumes a value of 0 or 4 to 12, and all radicals R$^3$ are those radicals which have a group according to formula (I).

Siloxanes preferably used in the process according to the invention are those of formula (II) in which variable 'a' assumes a value of 75 to 180 and variable 'c' assumes a value of 4 to 12 or variable 'a' assumes a value of 50 to 130 and variable 'c'=0 and at the same time all radicals R$^3$ are those radicals which have a group according to formula (I). The value for variable 'b' in these preferred embodiments is preferably 0.

Silicone (meth)acrylates which can be used are, for example, the product TEGO® RC 711,726, 902 and their methacrylate variants available from Evonik Industries AG.

Siloxanes which have at least one (meth)acrylate group of formula (I) that are used preferably in the process according to the invention are those which have this in the form of a radical from the group of the radicals

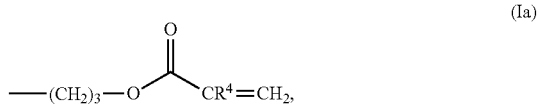
(Ia)

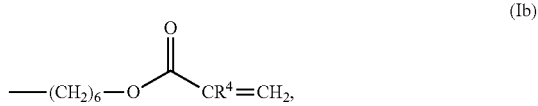
(Ib)

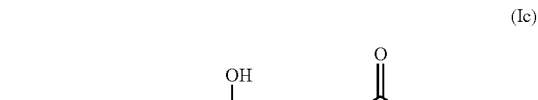
(Ic)

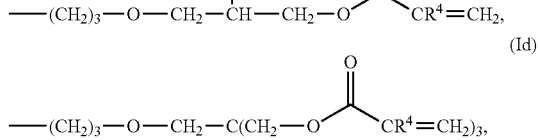
(Id)

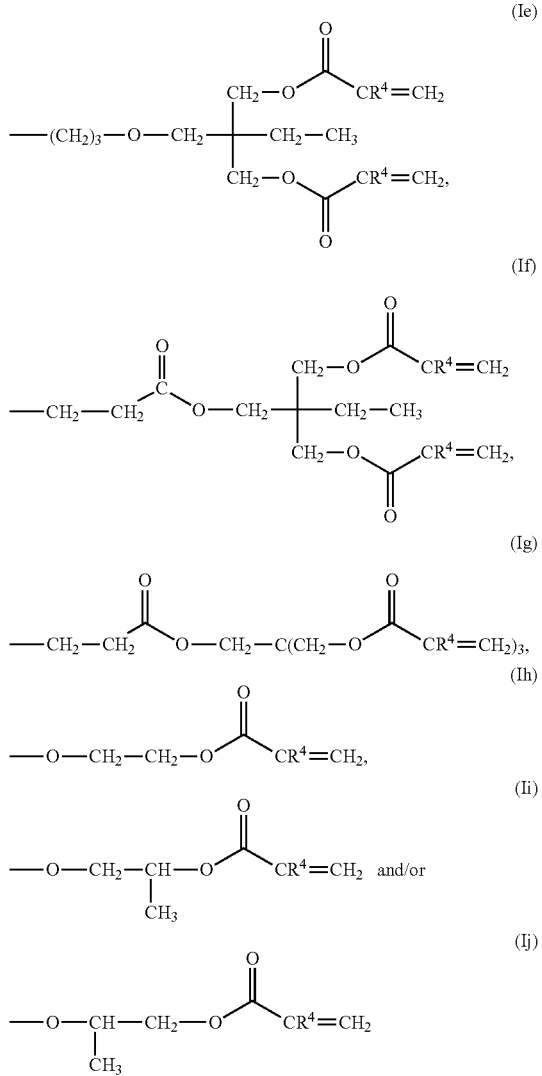

where $R^4$ is hydrogen or a methyl group, preferably a methyl group. More preferably, siloxanes which have at least one (meth)acrylate group of formula (I) are those which have this in the form of a radical selected from the group comprising the radicals with the formulae (Ib) and (Ie), where $R^4$ is a methyl group.

In the process according to the invention, the siloxanes containing at least one (meth)acrylate group of formula (I), in particular those of formula (II), can be used individually or as mixtures, in particular as statistical mixtures. In the process according to the invention, preference is given to using mixtures of siloxanes, in particular those of formula (II) in which the siloxanes differ as regards their structure and/or their molecular weight.

By virtue of using (particulate) solid-body emulsifiers, the process according to the invention can be used to produce particles, in particular those of the core/shell type. Such particles have the polymerized siloxane in the core and the particulate emulsifiers as shell.

It may be advantageous if, before step b), comonomers, in particular comonomers having ethylenically or vinylically unsaturated groups, are added to the organic phase. Such comonomers can be, e.g., mono- or poly-(meth) acrylated, organic mono- or oligomers, as are commercially available for example also under the group names LAROMER® (BASF AG), EBECRYL® (Cytec Surface Specialties) or DESMOLUX® (Bayer Material Science). Preference is given to using (meth)acrylates of long-chain fatty alcohols, such as, e.g., lauryl methacrylate, myristyl methacrylate, cetyl methyacrylate or stearyl methacrylate. Ethylenically mono- or polyunsaturated organic mono- or oligomers are to be understood as meaning organopolysiloxanes carrying ethylenically unsaturated, preferably vinylic groups. Preferably, the addition of the further comonomers takes place before step a).

After the polymerization in step b) is complete, the organic comonomers can either be incorporated by covalent reaction into the polysiloxane (meth)acrylate network, or alternatively the organic comonomers can be present as an independent network. Mixed forms of these described limiting cases are likewise possible and form part of this invention.

The solid-body emulsifiers used in the process according to the invention are preferably those which are selected from the group of (semi-)metal oxides, mixed oxides, nitrides, hydroxides, carbonates or silicates. Preferred solid-body emulsifiers have metal oxide and/or a semimetal oxide. Particularly preferred solid-body emulsifiers are based on silicon dioxide.

In order to support the formation of an emulsion in which the inner phase is the organic phase, it may be advantageous to use those solid-body emulsifiers which have a contact angle of less than 90° at the water/organic phase interface in the process according to the invention. The contact angle can be determined as described by Bernard Paul Binks, Lucio Isa and Andrew Terhemen Tyowua in "Direct Measurement of Contact Angles of Silica Particles in Relation to Double Inversion of Pickering Emulsions" in document dx.doi.org/10.1021/la4006899 Langmuir 2013, 29, 4923-4927.

It may be advantageous if solid-body emulsifiers are used which are hydrophobicized or partially hydrophobicized. Suitable hydrophobicizing agents are, e.g., compounds selected from the group of silanes, siloxanes, quaternary ammonium compounds, cationic polymers and fatty acids or anions thereof. If partially hydrophobicized solid-body emulsifiers are used, preference is given to using those which are not Janus particles (but have a uniform distribution of the hydrophobicized and non-hydrophobicized regions on the surface of the solid-body emulsifiers). Particularly preferred solid-body emulsifiers have silicon dioxide and are at least partially hydrophobicized, with preference being given to partially hydrophobicized particles which are not Janus particles.

The solid-body emulsifiers used in the process according to the invention preferably have an average (volume-average) particle size (primary particle size) of >100 nm to <200 nm. The particle size of the solid-body emulsifiers can be determined in the known manner. The average primary particle size is preferably determined by dynamic light scattering. For this, for example, the ZetaSizer Nano ZSP from Malvern can be used. Alternatively, the particle size can be determined by the visual evaluation of an image created by transmission electron microscopy.

The particulate emulsifiers (solid-body emulsifiers) can be used in the process according to the invention as they are or in the form of dispersions or sols, in particular aqueous dispersions or sols.

The amount of particulate emulsifiers used is preferably 2 to 30% by weight, preferably 5 to 25% by weight, particularly preferably 7.5 to 20% by weight, based on the siloxanes used containing at least one (meth)acrylate group of formula (I).

It may be advantageous if, in step a) of the process according to the invention, the preparation of the emulsion is carried out with the addition of one or more coemulsifiers. Coemulsifiers which can be used in the process according to the invention are in particular those compounds which interact with the solid-body emulsifier particles, preferably which, as a result of electrostatic interaction, attach evenly to the surface of the solid-body emulsifier particles and in so doing lead to a (partial) hydrophobicization of the emulsifier particles. In the process according to the invention, coemulsifiers which can be used are in particular compounds selected from the group of cationic surfactants. Cationic coemulsifiers which can be used are in particular cationic ammonium compounds. Such compounds are available, e.g., under the trade names VARISOFT® 470 P, VARISOFT® TC-90, VARISOFT® 110, VARISOFT® TA-100, ADOGEN® 442-100 P, ADOGEN® 432, ADOGEN® 470, ADOGEN® 471, ADOGEN® 464, VARIQUAT® K 300, VARIQUAT® B 343, VARIQUAT® 80 ME, REWOQUAT® 3690, REWOQUAT® WE 15, REWOQUAT® WE18, REWOQUAT® WE 28 or REWOQUAT® CR 3099 from Evonik Industries AG. In the process according to the invention, preference is given to using VARISOFT® TA-100 or VARISOFT® PATC (both available from Evonik Industries AG), particularly preferably VARISOFT® PATC as cationic coemulsifier. In the process according to the invention, even more preference is given to producing no silicone (meth)acrylate particles in whose preparation no cetyltrimethylammonium bromide or chloride is/has been used.

Optionally, further components can be added to the organic phase in step a). The further components can be dissolved or dispersed in the organic phase or the mixture in step a). Based on the organic phase, the further components can preferably be present in a concentration of 0.01 to 99% by weight, preferably 0.1 to 80% by weight and particularly preferably from 1 to 50% by weight. Such further components can be functional components or non-functional components. Further components which can be used are in particular dispersible solids, such as, e.g., inorganic particles and/or fibres, such as, e.g., those of metal oxides, mixed oxides, nitrides, hydroxides, carbonates, silicates, pigments, carbon blacks, elements or alloys, and/or organic particles and/or fibres, such as, e.g., those of silicone resins, silicones or organic polymers or biopolymers, preferably with the proviso that the fillers are different from the emulsifiers used. Dispersible solids can for example be precipitated silica, diatomaceous earth (kieselgur), fumed silica, quartz flour, titanium dioxide, zinc oxide, cerium oxide, iron oxide, carbon black, graphite, carbon nanotubes or -fibres, alumosilicates, alkaline earth metal carbonates, aluminium trihydroxide, magnesium dihydroxide or other solids that are customary and known from the prior art, as well as each of the specified substances following surface modification with organosilicon compounds such as trimethyl chlorosilane, hexamethyl disilazane, (meth)acryloxypropyltrialkoxysilanes, aminopropyltrialkoxysilanes, polydimethylsiloxanes, polysiloxanes which carry Si—H groups, or pure carboxylic acids, chelating agents or fluoropolymers. These solids can serve, for example, as fillers for achieving certain mechanical properties, as UV stabilizers, as pigments, as antistatic additives or for achieving ferromagnetic properties.

In the process according to the invention, the organic phase can also contain substances which can optionally be released from the particles, preferably over a prolonged period. Such substances may be, e.g., cosmetic oils and active ingredients, fragrances, pharmaceutical active ingredients, cosmetic active substances, antimicrobial active ingredients, also, for example, silver and silver-containing compounds, as well as dyes and preservatives.

In some embodiments, it may be advantageous if in step a) of the process according to the invention the emulsion produced in step a) comprises 10 to 40% by weight of organic phase, particularly preferably 15 to 35% by weight, based on the emulsion.

In other embodiments, it may be advantageous if in step a) of the process according to the invention an emulsion is generated whose average droplet size is adjusted from 0.01 to 1000 µm, preferably 0.1 to 500 µm and particularly preferably from 1 to 100 µm.

In yet other embodiments, it may be particularly advantageous if in step a) of the process according to the invention the emulsion produced in step a) comprises 10-40% by weight of organic phase, particularly preferably 15-35% by weight, based on the emulsion, and the emulsion has an average droplet size of 0.01 to 1000 µm, preferably 0.1 to 500 µm and particularly preferably from 1 to 100 µm.

The droplet size can be estimated with the assistance of a light microscope (up to about 1 µm as lower limit) by measuring the smallest and largest droplet diameter in each case in the field of vision; in this connection there should be at least 10×10 drops in the field of vision. Furthermore, it is possible to determine the droplet size distributions by means of the methods of statistical and dynamic light scattering familiar to the person skilled in the art. The MasterSizer 3000 from Malvern, for example, can be used for this purpose. This is also the case for dispersions of fully polymerized particles; moreover, the particle size can be determined by electron micrographs via SEM or TEM and is familiar to the person skilled in the art.

Preferably, the emulsion in step a) is prepared by passing through the mixture comprising organic and aqueous phase and dispersing the mixture in at least one interaction chamber, preferably with a capillary thickness (internal diameter) of 50 to 500 µm, and preferably at a pressure of 50 to 1000 bar, preferably 100 to 800 bar, particularly preferably 200 to 600 bar and subsequent decompression of the mixture to ambient pressure, e.g., into a discharge reservoir. In this connection, preferably one of the aforementioned preferred droplet sizes is set. It may be advantageous if two or more serially connected interaction chambers are used. In this way, the desired droplet size can be adjusted more easily. The preparation of emulsions in interaction chambers is described in detail in U.S. Publication no. 2004-0063818 and DE 100 11 564, to which reference is expressly made. A suitable instrument for preparing the emulsions is supplied for example under the name Mikrofluidizer by Microfluidics.

In order to obtain an emulsion with droplet sizes in the preferred range, the droplets of which preferably have a spherical morphology, in the event of the addition of coemulsifiers, it may be advantageous to only add the coemulsifier or the coemulsifiers after a preemulsion V1 has been prepared in a part step a1). This preemulsion V1, e.g., can be obtained by emulsifying a mixture of siloxanes comprising (meth)acrylate groups of formula (I), water and emulsifier, preferably particulate emulsifier and particularly preferably nanoparticulate $SiO_2$ and even more preferably IDISIL Si5530 from Evonik Industries AG while applying strong shear forces, as is possible, e.g., with a rotor-rotor system. A suitable rotor-rotor system is supplied, e.g., as Co-Twister Homogenizer by Symex.

It may be particularly advantageous if, before the preparation of the preemulsion V1 in a part step a0), the radical initiator required for the subsequent reaction is dissolved in the siloxane used containing (meth)acrylate groups of formula (I). Suitable solubility promoters can optionally be used for this purpose.

To stabilize the preemulsion V1, the coemulsifier is added to this in a further part step a2). The coemulsifiers can be added as pure substance or in the form of a solution, e.g., an aqueous solution. By adding the coemulsifier to the preemulsion V1, the droplet size of the drops present in the preemulsion V1 can be quasi frozen. Droplet size distribution can thus be adjusted by the time of the addition of the cosurfactant. Inter alia, the droplet size distribution of the emulsion can be preadjusted by the addition amount of emulsifier and coemulsifier. Preferably, the weight ratio of particulate emulsifier to coemulsifiers is from 100:1 to 1:1, preferably from 50:1 to 3:1.

The stabilized preemulsion V2 obtained in step a2) is then dispersed in step a3) in a homogenizer with interaction chamber. Preferably, the emulsion in step a) is produced by passing through the mixture comprising organic and aqueous phase and dispersing the mixture in at least one interaction chamber, preferably with a capillary thickness (internal diameter) of 50 to 500 μm, and preferably at a pressure of 50 to 1.000 bar, preferably 100 to 800 bar, particularly preferably 200 to 600 bar and subsequent decompression of the mixture to ambient pressure, e.g., into a discharge reservoir. In this regard, preferably one of the aforementioned preferred droplet sizes is set. It may be advantageous if two or more serially connected interaction chambers are used. In this way, the desired droplet size can be adjusted particularly easily. A suitable homogenizer is supplied, for example, under the name Mikrofluidizer by Microfluidics.

Preferably, in step a3) of the process according to the invention, interaction chambers are used, of which at least one has a capillary thickness of 100 to 300 μm. In step a) of the process according to the invention, particular preference is given to using interaction chambers, of which at least one, preferably all, have at least one diverting bend.

By virtue of carrying out part steps a1) to a3) and using a homogenizer with interaction chamber in part step a3), it is particularly easy to produce spherical droplets with a desired droplet size distribution.

The polymerization of the emulsion prepared in process step a) is initiated in step b) by one of the radical initiators added to the emulsion which is characterized in that it is more soluble in the organic phase than in the aqueous phase. The radical initiator is preferably added in a concentration of 0.05 to 2% by weight, preferably 0.1 to 1% by weight and particularly preferably >0.15 to 0.6% by weight, based on the inner (organic) phase. As described above, it may be advantageous if the radical initiator used in process step b) is added to the organic phase before or during process step a). The full polymerization preferably takes place in the form of a suspension polymerization.

Radical initiators which can be used are customary compounds suitable as radical initiators, preferably organic radical initiators. Preferably used radical initiators are those which form radicals by supplying thermal energy. Particularly preferably used radical initiators are those which, after the radical start, become compounds which are tolerable in cosmetic products, such as, e.g., hydrocarbons, alcohols or acids having 8 to 30 carbon atoms. Radical initiators which can be used are in particular peroxides which are derived from organic acids, in particular fatty acids. Among these compounds, which are also known as diacyl peroxides, preference is given to lauroyl peroxide (dilauroyl peroxide), decanoyl peroxide and isononanoyl peroxide. Particular preference is given to using dilauroyl peroxide as radical initiator. The initiation preferably takes place by increasing the temperature. The radical initiators used are preferably not redox systems. Optionally, it may be advantageous if the radical initiators are used in combination with radical transfer agents. Preferred radical transfer agents can be, e.g., acetylacetone, acetone or the like. Such systems are well known as radical initiators and are prior art in the field of emulsion polymerization.

Process step b) is preferably carried out at elevated temperature. Preferably, process step b) is carried out with stirring and preferably under protective gas/inertization. Alternatively, the polymerization in step b) can be carried out in a conventional manner as described in the prior art.

After carrying out polymerization step b), it may be advantageous to separate off the resulting particles from the suspension. For this, e.g., the water can be removed by customary methods, for example, by filtration or centrifugation. In order to increase the rate of the drying operation, it may be advantageous to wash the particles in one of the wash cycles, e.g., with ethanol.

It may be advantageous if the particles are surface-modified after the synthesis. The surface modification can take place by customary methods. The surface modification can be carried out with organic and/or inorganic as well as with charged and/or uncharged substances.

It may be particularly advantageous if the modifying agent has at least one functional group which can enter into a covalent, ionic or coordinate bond or hydrogen bridge bonds with the surface to be modified.

Besides the at least one functional group which can enter into a bond with the surface of the core/shell silicone particle, the modifying agent can additionally have further radicals which modify the properties of the particles. Such radicals, or else parts thereof, can, for example, be hydrophobic or hydrophilic or carry one or more functional groups in order, in this way, to make the silicone particles compatible with the surrounding medium.

The particles according to the invention obtainable by polymerization of a siloxane which has at least one (meth) acrylate group of formula (I)

$$—O—C(O)—CR=CH_2 \quad (I)$$

where R=—H or —$CH_3$, are characterized in that the siloxane (used) has an average molar ratio of groups of formula (I) to Si atoms of less than 0.1. Preferably, the particles according to the invention are obtainable by a process as described above.

Preferably, the particles according to the invention are obtainable by a process comprising the steps:

Producing an emulsion from an aqueous phase and an organic phase, wherein the organic phase has at least one siloxane which has at least one (meth)acrylate group of formula (I)

$$—O—C(O)—CR=CH_2 \quad (I)$$

where R=—H or —$CH_3$,
with the addition of at least one solid-body emulsifier and mixing of the two phases, where the organic phase forms the inner phase of the emulsion, and fully polymerizing the inner phase in the presence of a radical initiator which is more soluble in the organic phase than in the aqueous phase, which is characterized in that the siloxane has an average molar ratio of groups of formula (I) to Si atoms of less than 0.1, in particular by the process according to the invention described above.

The particles according to the invention preferably have a polymer which has been obtained by polymerization of siloxanes containing at least one (meth)acrylate group of the formula (I) and optionally other monomers optionally in the presence of further components such as, for example, fillers, auxiliaries or active substances etc. in the presence of a radical initiator, in particular an organic radical initiator.

The particles according to the invention preferably have an average particle size $d_{50}$ from 1 to 40 μm, preferably from 3 to 20 μm, particularly preferably 5 to 15. Preferred particles have a particle size $d_{90}$ of 10 to 100 μm, preferably of 15 to 80 μm, particularly preferably 40 to 70 μm. The particle size $d_{10}$ of the particles according to the invention is preferably from 0.5 to 15 μm, preferably from 1 to 10 μm, particularly preferably 2 to 7.5 μm. More preferably, the particles according to the invention are those which satisfy all of the aforementioned values for $d_{10}$, $d_{50}$ and $d_{90}$, in particular the values given as being most preferred. The determination of the values $d_{10}$, $d_{50}$ and $d_{90}$ takes place preferably by statistical laser diffraction methods familiar to the person skilled in the art. For this, the MasterSizer 3000 with attached Aero S dry dispersing unit from Malvern can for example be used.

The particles according to the invention can have (meth) acrylate compounds that have not fully reacted but are covalently bonded to the polymer (compounds which have a free group of the formula (I)), preferably in a concentration of less than 5000 ppm by mass (wppm), preferably less than 3000 ppm by mass, particularly preferably less than 1500 ppm by mass, based on the particle. The fraction of non-fully reacted (meth)acrylate compounds can be determined, for example, by hydrolysis of the particles in ethanolic potassium hydroxide solution and subsequent determination of the released (meth)acrylic acid by means of HPLC.

Preferred particles according to the invention are those which have a core/shell structure (so-called silicone (meth) acrylate composite particles). In these, a shell, where the shell is preferably formed by particulate emulsifiers, surrounds the inner core which has the polymerized silicone (meth)acrylate. Particularly preferred silicone (meth)acrylate particles are those in which the shell is formed from the aforementioned inorganic particles whose surface is preferably modified.

Preferred particles can be those in which the shell is modified. Such a modification can be carried out, e.g., with cationic substances, such as organic ammonium ions or cationic polymers, cationic siloxanes, organic polymers such as, for example, polyacrylates, carboxylic acids or carboxylic acid anions, chelating agents, diketones, siloxanes or condensed silanes as described above. The surface modification can be bonded physically or chemically to the polymer particle. Furthermore, the surface modifiers can carry functional groups such as, for example, in the case of the use of functional silanes. The surface modifiers can consist of discrete molecules, but can also be crosslinked.

Besides the silicone (meth)acrylate, the particles can possibly comprise comonomers used during the polymerization. These comonomers can be completely or partially incorporated by reaction into the polysiloxane (meth)acrylate network or else be in the form of an independent network. Mixed forms of these described limiting cases are likewise possible and form part of this invention.

It may be advantageous if the particles have further components which are not constituents which have originated from the emulsifiers, monomers or comonomers. Based on the polysiloxane (meth)acrylate polymers, the particles have these further components preferably in a concentration of 0.01 to 99% by weight, preferably from 0.1 to 80% by weight and particularly preferably from 1 to 50% by weight. Such further components can be functional components or non-functional components. Further components which may be present in the particles are in particular solids, such as, e.g., inorganic particles and/or fibres, such as, e.g., those of metal oxides, mixed oxides, nitrides, hydroxides, carbonates, silicates, pigments, carbon blacks, elements or alloys, and/or organic particles and/or fibres, such as, e.g., those of silicone resins, silicones or organic polymers or biopolymers, preferably with the proviso that the fillers of the emulsifiers used are different. Further components can be selected in particular from precipitated silica, diatomeous earth (kieselgur), fumed silica, quartz flour, titanium dioxide, zinc oxide, cerium oxide, iron oxide, carbon black, graphite, carbon nanotubes or -fibres, alumosilicates, alkaline earth metal carbonates, aluminium trihydroxide, magnesium dihydroxide and other solids that are customary and known from the prior art, as well as each of the specified substances following surface modification with organosilicon compounds such as trimethylchlorosilane, hexamethyl disilazane, (meth)acryloxypropyltrialkoxysilanes, aminopropyltrialkoxysilanes, polydimethylsiloxanes, polysiloxanes which carry Si—H groups, or pure carboxylic acids, chelating agents or fluoropolymers. These solids can serve for example as fillers for achieving certain mechanical properties, as UV stabilizers, as pigments, as antistatic additives or for achieving ferromagnetic properties.

The further components can be added subsequently to the already polymerized particles by means of swelling and diffusion. This can also take place with the assistance of a solvent, which is removed again afterwards. However, it is also possible to add the further components during the preparation process (see above). In particular, the further components in step a) of the process according to the invention can be added to the organic phase. The further components can be dissolved in the polymer matrix or else bonded to the matrix by an optionally labile covalent bond.

The silicone (meth)acrylate particles according to the invention can include one or more substances, in particular selected from the aforementioned further components, which can be released from the particles. The release can take place in the corresponding applications over a prolonged period. The release can take place, e.g., by means of diffusion or hydrolysis reactions and subsequent diffusion.

Substances that are to be released that can be present in the particles are, for example, cosmetic oils and active ingredients, fragrances, pharmaceutical active ingredients, antimicrobial active ingredients, also for example silver and silver-containing compounds, as well as dyes and preservatives. These substances can be present either in dissolved form or else embedded in the silicone (meth)acrylate matrix or else bonded to the silicone (meth)acrylate matrix by means of a labile chemical bond.

The particles according to the invention or produced according to the invention can be used alone or in a mixture with further particles, pigments and/or further customary additives, e.g., in the form of powders or dispersions, in cosmetic or pharmaceutical preparations or in care compositions.

The preparation of the dispersions with the particles according to the invention can take place by means of the customary methods corresponding to the prior art, although it is advantageous to further process the particles resulting after the polymerization according to step b) of the process according to the invention and washing with alcohol(s) or water without prior drying to give, for example, aqueous dispersions. This is also possible if, for example, a desired surface modification can take place directly from aqueous or alcoholic phase, which has a favorable effect on the process economics.

The silicone (meth)acrylate particles according to the invention and/or dispersions comprising these can be used as additives in cosmetics and toiletries, e.g., as matting agents, as absorbers for skin sebums or for producing a pleasant, velvety-silky skin feel, as mild abrasive in washing and care formulations, and as formulation constituents or carrier materials that release active ingredients or auxiliaries over a prolonged period.

The composition according to the invention is preferably a cosmetic or pharmaceutical preparation or a care composition, in particular a care composition for skin and/or hair, preferably human skin and/or hair.

The present invention thus also provides care and cleaning formulations, in particular for skin and skin appendages, and also for the home and industry, in particular cosmetic formulations, with these preferably being selected from the group of skin and hair treatment compositions, for example formulations for skin care or decorative cosmetics, shampoos with or without pronounced conditioner effect, liquid soaps and shower gels, comprising particles according to the invention.

A formulation preferred according to the invention comprises the particles according to the invention in an amount from 0.1% by weight to 99% by weight, preferably in an amount of 0.5% by weight to 50% by weight, particularly preferably in an amount of 1.0% by weight to 20% by weight, where the % by weight are based on the total formulation.

Cosmetic care and cleaning formulations according to the invention can for example comprise at least one additional component selected from the group of:
surfactants,
emollients,
emulsifiers,
coemulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents,
solvents,
UV filters,
electrolytes,
multifunctional additives,
moisturizing substances.

Substances which can be used as exemplary representatives of the individual groups are known to the person skilled in the art and can be found for example in EP2273966A1. This patent application is herewith incorporated as reference and thus forms part of the disclosure.

As regards further optional components and the amounts of these components used, reference is made expressly to the relevant handbooks known to the person skilled in the art, e.g., K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Preferred formulations according to the invention are aqueous, surface-active formulations; these comprise preferably at least 50% by weight, preferably 70% by weight of water and at least one surfactant.

Besides the particles according to the invention, in particular nonionic surfactants of the component selected from the group consisting of glycerol mono- and diesters and sorbitan mono- and diesters of saturated and unsaturated fatty acids, alkyl mono- and oligoglycosides, partial esters based on linear, branched, unsaturated or saturated fatty acids, ricinoleic acid, and 12-hydroxystearic acid and glycerol, polyglycerol, pentaerythritol, dipentaerythritol, sugar alcohols (e.g., sorbitol), alkyl glucoside (e.g., methyl glucoside, butyl glucoside, lauryl glucoside, cocoglucoside), and polyglucosides (e.g., cellulose), mono-, di- and trialkylphosphates and salts thereof, citric acid esters such as, e.g., glyceryl stearate citrate, glyceryl oleate citrate and dilauryl citrate, and glyceryl caprylate, polyglyceryl caprylate, polyglyceryl caprate and mixtures of these surfactants are present in the formulations according to the invention.

Preferred cleaning and care formulations according to the invention for the home and industry are textile-softening formulations and textile-care washing or cleaning compositions, dishwashing detergents, household cleaners, disinfectants, disinfectant cleaners, foam cleaners, floor cleaners, carpet cleaners, upholstery cleaners, floor care products, marble cleaners, parquet cleaners, stone and ceramic floor cleaners, wipe care compositions, stainless steel cleaners, glass cleaners, plastic cleaners, sanitary cleaners, wood cleaners, leather cleaners, detergents, laundry care compositions, disinfectant detergents, standard detergents, gentle detergents, wool detergents, fabric softeners and impregnating compositions, with dishwashing detergents and household cleaners, in particular hand dishwashing detergents, being particularly preferred.

Particularly preferred cleaning and care formulations according to the invention for the home and industry additionally comprise one or more substances from the group of surfactants, builders, bleaches, bleach activators, enzymes, perfumes, perfume carriers, fluorescent agents, dyes, foam inhibitors, silicone oils, antiredeposition agents, optical brighteners, greying inhibitors, shrink preventers, anticrease agents, colour transfer inhibitors, antimicrobial active ingredients, germicides, fungicides, antioxidants, preservatives, corrosion inhibitors, antistats, bittering agents, ironing aids, phobicization and impregnation agents, swelling and slip-resist agents, neutral filling salts, and UV absorbers.

In particular, the cleaning and care formulations according to the invention for the home and industry can comprise between 0.001 and 90% by weight, particularly preferably 0.01 to 45% by weight, of one or more of the further ingredients mentioned here, where the % by weight refer to the total formulation.

Examples of surfactants that can be used are described in WO 2007/115872, page 17, line 28 to page 21, line 24.

Examples of builder substances, builders, bleaches, bleach activators, bleach catalysts and enzymes are described in WO 2007/115872, page 22, line 7 to page 25, line 26.

Antiredeposition agents, optical brighteners, greying inhibitors, transfer inhibitors are described by way of example in WO 2007/115872 on page 26, line 15 to page 28, line 2.

Examples of anticrease agents, antimicrobial active ingredients, germicides, fungicides, antioxidants, preservatives, antistats, ironing aids, UV absorbers are described in WO 2007/115872 on page 28, line 14 to page 30, line 22. Their explicit disclosure content in this regard forms part of this disclosure by virtue of this reference.

The examples listed below illustrate the present invention by way of example, without any intention of restricting the invention, the scope of application of which is apparent from the entirety of the description and the claims, to the embodiments specified in the examples.

EXAMPLES

Comparative Example 1

Particles of silicone methacrylate with an average molar ratio of methacrylate groups to Si atoms of 0.055; with redox radical initiator 163.25 g of demineralized water and 62.50 g of IDISIL SI-5530 were mixed and adjusted to pH 7 with hydrochloric acid. The mixture was introduced into a beaker and, with stirring, 125 g of a silicone methacrylate of the formula (I) where $a=170$, $b=0$, $c=8$, $R^1=CH_3$, $R^3=R'=-C_6H_{12}-O-C(O)-C(CH_3)=CH_2$ were added. The mixture was sheared using a Dispermat at 5000 rpm for 30 minutes. Then, 2.25 g of 5% strength by weight VARISOFT® PATC solution were added dropwise and the mixture was sheared for a further 30 minutes at 5000 rpm. The stabilized preemulsion was admixed with 45 g of dipotassium hydrogen phosphate dissolved in 27.0 g of demineralized water and sheared again at 5000 rpm for 30 minutes. The resulting emulsion was homogenized by passing through a homogenizer (in the examples in each case a microfluidizer from Microfluidics was used) with an interaction chamber with 200 μm diameter at 800 bar pressure.

For the polymerization, 325 g of the emulsion were placed into a 1 l round-bottomed flask and heated to 80° C. under a nitrogen atmosphere. With constant stiffing, a solution of 12.5 g of ammonium peroxodisulphate in 40 ml of demineralized water was slowly added dropwise to the heated solution. Then, 7.5 g of a 39% strength by weight sodium hydrogensulphite solution was added. The reaction mixture was stirred for a further 2 h at 80° C. After the polymerization, a considerable brown colouration of the reaction mixture was observed.

For bleaching the cured dispersion, at 80° C. 15 g of a 30% strength hydrogen peroxide were added with continuous stiffing, during which a considerable lightening of the reaction mixture was established. Then, the particle dispersion was slowly cooled to room temperature and filtered. The resulting particles were washed five times with 150 ml of water in each case and dried to constant mass in a vacuum drying cabinet at 50° C. By means of electron microscopic viewing of the particles, it was possible to determine an average size of the particles of approximately 10 μm. It was noticeable here that the particles had indentations ("dimples").

To determine the fraction of methacrylate groups which have not reacted but are covalently bonded to the particles, these were hydrolyzed by alkaline ester cleavage and the methacrylic acid released during this was quantified by means of HPLC. For this, 0.5 g of the particles were boiled for 1 hour at reflux in 25 ml of 1 normal ethanolic potassium hydroxide solution, 5 ml of $H_2O$ and 1 ml of diethylene glycol monoethyl ether. The hydrolyzate was transferred with a small amount of ethanol to a 50 ml measuring flask and topped up. Then, the sample was diluted with water in the ratio 1:10 and at the same time adjusted to pH 2 with concentrated sulphuric acid. The subsequent chromatographic separation of the sample was carried out by means of RP HPLC with UV detection (HPLC system: Agilent 1100, column: Macchery & Nagel Pyramid C18). Here, a residual methacrylate content of 11 000 ppm was ascertained.

Example 1 According to the Invention

Particles of silicone methacrylate with an average molar ratio of methacrylate groups to Si atoms of 0.055; with oil-soluble radical initiator 228.5 g of demineralized water and 50.0 g of IDISIL SI 5530 were mixed and adjusted to pH 7 with hydrochloric acid. The mixture was introduced into a beaker and, with stirring, 100 g of a silicone methacrylate of the formula (I) where $a=170$, $b=0$, $c=8$, $R^1=CH_3$, $R^3=R'=-C_6H_{12}-O-C(O)-C(CH_3)=CH_2$, in which 0.3 g of lauryl peroxide have been dissolved beforehand, were added. Then, the mixture was sheared using a Dispermat at 5000 rpm for 30 minutes. Next, 5.5 g of a 1% strength by weight VARISOFT® PATC solution were slowly added dropwise and the mixture was sheared for a further 30 minutes at 5000 rpm. The resulting preemulsion was homogenized by passing through a homogenizer with an interaction chamber with 200 μm diameter at 800 bar pressure.

For the polymerization, the emulsion was transferred to a 500 ml round-bottomed flask and then a stream of nitrogen was introduced for 45 min with stirring. The reaction mixture was then heated to 80° C. and kept at this temperature for 3 h with gentle stirring. After cooling, the thus cured particle dispersion was filtered. The resulting particles were washed twice with water and then dried to constant mass in a vacuum drying cabinet at 50° C. By means of electron microscopic viewing of the particles, an average size of the particles of approximately 10 μm could be ascertained. In contrast to the particles described in Comparative Example V1, the particles had a "more spherical" morphology and no indentations on the particles could be found.

To determine the fraction of methacrylate groups that have not reacted but are bonded covalently to the particles, the analytical method described in Comparative Example V1 was used. Here, a residual methacrylate content of 1040 ppm was found. This is thus more than a factor of ten less than the ascertained residual methacrylate content of the particles described in Comparative Example 1.

Comparative Example V1

Particles of silicone methacrylate with an average molar ratio of methacrylate groups to Si atoms of 0.25; with oil-soluble radical initiator 228.5 g of demineralized water and 50.0 g of IDISIL SI 5530 were mixed and adjusted to pH 7 with hydrochloric acid. The mixture was introduced into a beaker and, with stirring, 100 g of a silicone methacrylate of the formula (I)

where a=15, b=0, c=5, $R^1$=$R^3$=$CH_3$, R'=$(CH_2)_3$—O—$CH_2$—CH(OH)—$CH_2$—O—C(O)—C($CH_3$)=$CH_2$, in which 0.3 g of lauryl peroxide were dissolved beforehand, were added. Then, the mixture was sheared using a Dispermat at 5000 rpm for 30 minutes. Next, 5.5 g of a 1% strength by weight VARISOFT® PATC solution were slowly added dropwise and the mixture was sheared for a further 30 minutes at 5000 rpm. The resulting preemulsion was homogenized by passing through a homogenizer with an interaction chamber with 200 µm diameter at 800 bar pressure.

For the polymerization, the emulsion was transferred to a 500 ml round-bottomed flask and then a stream of nitrogen was introduced for 45 min with stirring. The reaction mixture was then heated to 80° C. and kept at this temperature for 3 h with gentle stirring. After cooling, the thus cured particle dispersion was filtered. The resulting particles were washed twice with water and then dried to constant mass in a vacuum drying cabinet at 50° C.

Example 2 According to the Invention

Particles of silicone methacrylate with an average molar ratio of methacrylate groups to Si atoms of 0.047; with oil-soluble radical initiator 228.5 g of demineralized water and 50.0 g of IDISIL SI 5530 were mixed and adjusted to pH 7 with hydrochloric acid. The mixture was introduced into a beaker and, with stirring, 100 g of a silicone methacrylate of the formula (I) where a=83, b=0, c=0, $R^1$=$CH_3$, $R^3$=$(CH_2)_3$—O—$CH_2$—C($CH_2$—O—C(O)—C($CH_3$)=$CH_2$)$_2$—$CH_2$—$CH_3$, in which 0.3 g of lauryl peroxide were dissolved beforehand, were added. Then, the mixture was sheared using a Dispermat at 5000 rpm for 30 minutes. Next, 5.5 g of a 1% strength by weight VARISOFT® PATC solution were slowly added dropwise and the mixture was sheared for a further 30 minutes at 5000 rpm. The resulting preemulsion was homogenized by passing through a homogenizer with an interaction chamber with 200 µm diameter at 800 bar pressure.

For the polymerization, the emulsion was transferred to a 500 ml round-bottomed flask and then a stream of nitrogen was introduced for 45 min with stirring. The reaction mixture was then heated to 80° C. and kept at this temperature for 3 h with gentle stirring. After cooling, the thus cured particle dispersion was filtered. The resulting particles were washed twice with water and then dried to constant mass in a vacuum drying cabinet at 50° C.

The majority of the formulation examples listed below are emulsions of the oil-in-water (O/W) type or water-in-oil (W/O) type. These can be produced by customary methods known to the person skilled in the art using typical stirring units. W/O emulsions are preferably produced by slowly stirring the water phase into the oil phase with subsequent homogenization. In the case of the described O/W emulsions, oil and water phase are preferably combined without stirring and then homogenized. This can be performed in a cold-cold process or in a hot-hot process in which the homogenization takes place at about 70° C. The silicone (meth)acrylate particles according to the invention can be processed in principle in any stage of the process. In most of the example formulations, either the incorporation into the finished emulsion was carried out at temperatures <60° C. or the silicone (meth)acrylate particles were introduced directly at the start of the emulsion preparation together with the oil phase.

The nomenclature on the subject "incorporability" used for the assessment of the emulsion comparative examples is based on the following requirements. Under identical conditions as far as time of addition of the silicone (meth)acrylate particles and utilization of shearing units and rates is concerned, an easy incorporability describes no unusual effort for producing the formulation and the result is a uniform distribution of the silicone (meth)acrylate particles without troublesome agglomerates. If the incorporation is difficult, when using the same shearing unit and the same shearing rate, a longer shearing input has to be provided in order to arrive at an agglomerate-free formulation, or particle agglomerates cannot be incorporated without the agglomerates which affect the sensory properties.

The nomenclature on the subject "stability" used for the assessment of the emulsion comparative examples is based on the following requirements. If the stability is assessed as "good", this means that such an emulsion is stable for at least one month at room temperature, −5° C. and 40° C. "Stable" means here that no oil or water separation at all occurs, that the appearance of the emulsion remains homogeneous and that no significant changes in viscosity, colour or odour occur in the emulsion.

The skin feel of the cosmetic formulations described in the following examples was determined by a panel. At least five people compared the sensory properties of the cosmetic formulations and of the respective comparison formulation without knowing the composition. The properties are listed which the majority of the people described as preferable.

Example 3 and Comparison Example V3

The formulations given in Table 1a were prepared. The evaluation of the formulations was carried out with regard to their incorporability, stability, appearance and skin feel and is given in Table 1b.

TABLE 1a

Formulations re Example 3 and Comparative Example V3, oil-in-water care cream

|   |   | Example | |
|---|---|---|---|
|   |   | 3 | V3 |
| A | TEGO ® Care 165 (Evonik Industries AG) (Glyceryl stearate); PEG-100 stearate) | 6.0% | 6.0% |
|   | Stearyl alcohol | 3.0% | 3.0% |
|   | Mineral oil | 4.0% | 4.0% |
|   | Ethylhexyl palmitate | 4.0% | 4.0% |
| B | Glycerol | 3.0% | 3.0% |
|   | Water | 75.0% | 75.0% |
| C | Silicone methacrylate particles from Ex. 1 according to the invention | 5.0% |   |
|   | Silicone methacrylate particles from Comparative Ex. V1 |   | 5.0% |
| Z | Methylparaben, ethylparaben, methylisothiazolinone, perfume | q.a. | q.a. |

TABLE 18b

Results of Example 3 and Comparative Example V3, oil-in-water care cream

|   | Example | |
|---|---|---|
|   | 3 | V3 |
| Incorporability | Easy, agglomerates can be readily separated off by shearing | More difficult than for Example 3, separation of the agglomerates takes longer |

TABLE 18b-continued

Results of Example 3 and Comparative Example V3, oil-in-water care cream

| | Example | |
|---|---|---|
| | 3 | V3 |
| Stability | Good | Good |
| Appearance | White, homogeneous | White, homogeneous |
| Skin sensation | During application: velvety-silky, very smooth, not rough; 5 minutes after application: very smooth, powdery | During application: Velvety-silky, smooth; 5 minutes after application: somewhat rough, dry |

Example 4 and Comparison Example V4: Water-in-Oil Foundation

The formulations given in Table 2a were prepared. The evaluation of the formulations was carried out with regard to their stability, appearance and skin feel and is shown in Table 2b.

TABLE 2a

Water-in-oil foundation according to Example 4a, 4b and Comparative Example V4:

| | | Example | | |
|---|---|---|---|---|
| | | 4a | 4b | V4 |
| A | ABIL ® EM 90 (Evonik Industries AG) (Cetyl PEG/PPG-10/1 Dimethicone) | 3.0% | 3.0% | 3.0% |
| | Diethylhexyl carbonate | 10.0% | 10.0% | 10.0% |
| | Cyclopentasiloxane | 7.6% | 7.6% | 7.6% |
| | Ethylhexyl palmitate | 3.4% | 3.4% | 3.4% |
| | Iron oxide | 1.8% | 1.8% | 1.8% |
| | Titanium dioxide | 7.2% | 7.2% | 7.2% |
| | Talc | 2.0% | 2.0% | 2.0% |
| | Silicone methacrylate particles from Ex. 1 according to the invention | 2.5% | | |
| | Silicone methacrylate particles from Ex. 2 according to the invention | | 2.5% | |
| | Silicone methacrylate particles from comparative Ex. 2 | | | 2.5% |
| B | NaCl | 1.0% | 1.0% | 1.0% |
| | Glycerol | 2.0% | 2.0% | 2.0% |
| | Water | 59.5% | 59.5% | 59.5% |
| Z | Phenoxyethanol; methylparaben; ethylparaben, butylparaben; propylparaben, isobutylparaben, perfume | q.a. | q.a. | q.a. |

TABLE 2b

Water-in-oil foundation according to Example 4a, 4b and Comparative Example V4:

| | Example | | |
|---|---|---|---|
| | 4a | 4b | V4 |
| Incorporability | Easy, agglomerates can be readily separated by shearing | Easy, agglomerates can be readily separated by shearing | Easy, agglomerates can be readily separated by shearing |
| Stability | Good | Good | Good |
| Appearance | Brownish, homogeneous | Brownish, homogeneous | Brownish, homogeneous |
| Skin sensation | During application: velvety-silky, powdery very smooth, not rough; 5 minutes after application: very smooth, velvety-silky | During application: velvety-silky, powdery smooth, not rough; 5 minutes after application: smooth, velvety-silky | During application: powdery, rough; 5 minutes after application: rough, dry |

Further Formulation Examples

Example 5: O/W Serum with Cosmetic Active Ingredients According to Table 3

TABLE 3

O/W serum with cosmetic active ingredients according to Example 5

| | |
|---|---|
| Polyglyceryl-6 Stearate (and) Polyglyceryl-6 Behenate* | 2.5% |
| Caprylic/Capric Triglyceride** | 2.0% |
| Oleyl Erucate*** | 2.0% |
| Persea Gratissima (Avocado) Oil | 1.0% |
| Aqua; Ethylhexyl Stearate; Sodium Hyaluronate Crosspolymer; Polyglyceryl-4 Diisostearate/Polyhydroxystearate/Sebacate; Sodium Isostearate**** | 3.0% |
| Water | to 100% |
| Butylene glycol | 5.0% |
| Tetrapeptide-21; Glycerin; Butylene Glycol; Aqua***** | 2.0% |
| Hydrolyzed hyaluronic Acid****** | 0.1% |
| Silicone methacrylate particles from Ex. 1 | 1.00% |
| Xanthan Gum | 0.5% |
| Sodium Hydroxide (10% aq.) | 0.2% |
| Benzyl Alcohol, Benzoic Add, Sorbic Acid | 0.8% |
| Polyglutamic acid; Sclerotium Glucan; Betaine; Urea; Potassium Lactate******* | 3.0% |

*TEGO ® Care PBS 6 (Evonik Industries AG)
**TEGOSOFT ® CT (Evonik Industries AG)
***TEGOSOFT ® OER (Evonik Industries AG)
****Hyacare ® Filler CL (Evonik Industries AG)
*****TEGO ® PEP 4-17 (Evonik Industries AG)
******Hyacare ® 50 (Evonik Industries AG)
*******TEGO ® Smooth Complex (Evonik Industries AG)

Example 6: O/W Cream According to Table 4

TABLE 4

O/W cream according to Example 6

| | |
|---|---|
| Polyglyceryl-3 methylglucose distearate | 3.00% |
| Glyceryl stearate | 2.00% |
| Cetearyl alcohol | 1.00% |
| Ethylhexyl stearate | 10.00% |
| Decyl oleate | 9.00% |

TABLE 4-continued

| O/W cream according to Example 6 | |
| --- | --- |
| Silicone methacrylate particles from Ex. 1 | 1.50% |
| Glycerol | 3.00% |
| Water | to 100% |
| Sodium benzoate, potassium sorbate, phenoxyethanol, perfume | q.s. |

Example 7: Impregnation Solution for Wet Wipes According to Table 5

TABLE 5

| Impregnation solution for wet wipes according to Example 7 | |
| --- | --- |
| Ethylhexyl stearate, phenoxyethanol, sorbitan laurate, polyglyceryl-4 laurate, dilauryl citrate* | 5.70% |
| Cyclomethicone | 2.00% |
| Silicone methacrylate particles from Ex. 1 | 2.00% |
| Water | to 100% |
| Glycerol | 3.00% |
| Carbomer** | 0.10%. |
| Sodium hydroxide (10% in water) | q.s. |

*TEGO ® Wipe Flex (Evonik Industries AG)
**TEGO ® Carbomer 141 (Evonik Industries AG)

The impregnation solution can be used with the help of customary impregnation or spraying processes for producing cosmetic wet wipes (e.g., for baby care, make-up removers, cleansing wipes). For this, typically nonwovens are used, which generally have fibres of polyolefins, polyesters, celluloses, rayon, polyamides, polyester amides or polyvinyl alcohols or consist of these or which are composed of mixed fibres of these components.

Example 8: Make-Up Powder Foundation According to Table 6

TABLE 6

| Make-up powder foundation according to Example 8: | |
| --- | --- |
| Zinc stearate | 3.00% |
| Mica | 40.00% |
| Talc | 24.00% |
| Iron oxide | 5.00% |
| Silicone methacrylate particles from Ex. 1 | 10.00% |
| Titanium dioxide | 8.00% |
| Cetylethyl hexanoate | 2.00% |
| Squalane | 3.00% |
| Cetearylethyl hexanoate | 2.00%. |
| Mineral oil (30 mPas) | 2.00% |
| PEG/PPG-4/12 dimethicone | 1.00% |
| Aluminium starch octenylsuccinate | q.s. |
| Iron oxide | q.s. |
| Perfume | q.s. |

Example 9: Make-Up Foundation According to Table 7

TABLE 7

| Make-up foundation according to Example 9 | |
| --- | --- |
| Phenyltrimethicone | 14.00% |
| Ethylhexyl palmitate | 14.60% |

TABLE 7-continued

| Make-up foundation according to Example 9 | |
| --- | --- |
| Cetylethyl hexanoate | 5.00% |
| Carnauba wax | 4.70% |
| Stearoxydimethicone | 4.00% |
| PVP/eicosene copolymer | 1.00% |
| Cetylstearyl heptanoate | 2.85% |
| Covabead LH 85, polymethyl methacrylate particles | 3.00% |
| Silicon dioxide | 0.25%. |
| Zinc oxide | 7.00% |
| Nylon-12 | 2.00% |
| Talc Covasil 4.05 | 9.50% |
| Acrylate copolymer | 2.00% |
| Silicone methacrylate particles from Ex. 1 | 3.00% |
| Aluminium starch octenylsuccinate | 9.50% |
| Iron oxide | 3.10% |
| Titanium dioxide (and) dimethicone | 14.50% |

Example 10: Eyeshadow Formulation According to Table 8

TABLE 8

| Eyeshadow formulation according to Example 10 | |
| --- | --- |
| Cyclomethicone | to 100% |
| PPG-3 myristyl ether | 7.00% |
| Polyglyceryl-4 isostearate; cetyl PEG/PPG-10/1 dimethicone; hexyl laurate* | 1.00% |
| Dimethicone (20 mPas) | 2.50% |
| Cera alba | 4.50% |
| Carnauba wax | 2.00% |
| A-C Copolymer 400 (ethylene/VA copolymer) | 2.50% |
| Ozocerite | 5.80% |
| C18-36-acid triglyceride | 2.00% |
| Liquipar oil (isobutylparaben (and) isopropylparaben (and) butylparaben) | 0.20% |
| Silicone methacrylate particles from Ex. 1 | 4.00% |
| Titanium dioxide | 5.00% |
| Chromium oxide (green) | 10.00% |
| CI 77491 (and) aluminium powder (and) silicon dioxide | 5.00% |
| CI 77891 (and) CI 77288 (and) mica | 10.00% |

*ABIL ® WE 09 (Evonik Industries AG)

Example 11: O/W Sunscreen Lotion According to Table 9

TABLE 9

| O/W sunscreen lotion according to Example 11 | |
| --- | --- |
| Glyceryl stearate citrate | 3.00% |
| Cetearyl alcohol | 1.00% |
| Cetyldimethicone | 0.20% |
| $C_{12}$-$C_{15}$ alkyl benzoate | 4.80% |
| Triisostearin | 1.00% |
| Diethylhexyl carbonate | 6.00% |
| Titanium dioxide; trimethoxycaprylylsilane* | 3.00% |
| Tocopheryl acetate | 0.50% |
| Ethylhexyl methoxycinnamate | 5.00%. |
| Butylmethoxydibenzoylmethane | 2.50% |
| Carbomer | 0.20% |
| Xanthan | 0.40% |
| Sodium carboxymethylbetaglucan | 0.10% |
| Glycerol | 2.00% |
| Water | to 100% |
| Silicone methacrylate particles from Ex. 1 | 1.50% |
| Sodium hydroxide (10% in water) | q.s. |
| Perfume | q.s. |

*Tego ® Sun T 805 (Evonik Industries AG)

Example 12: AP/Deo Roll-on According to Table 10

TABLE 10

| Formulation according to Example 12 | |
|---|---|
| Steareth-2 | 2.20% |
| Steareth-20 | 1.00% |
| Cetearylethyl hexanoate | 2.00% |
| PPG-11 stearyl ether | 2.00% |
| Dimethicone | 0.50% |
| Polyglyceryl-3 caprylate | 0.50% |
| Aluminium chlorohydrate | 5.00% |
| Water | to 100% |
| Glycerol | 3.00% |
| Silicone methacrylate particles from Ex. 1 | 0.30%. |
| Perfume | q.s. |
| Citric acid (50% in water) | q.s. |
| Phenoxyethanol; ethylhexylglycerol | q.s. |

Example 13: Lipstick Formulation According to Table 11

TABLE 11

| Formulation according to Example 13 | |
|---|---|
| Cyclopentasiloxane | 34.00% |
| Behenoxydimethicone | 3.00% |
| Stearyldimethicone | 10.00% |
| Polyisobutene | 5.00% |
| Phenyltrimethicone | 8.00% |
| Isododecane | 4.00% |
| Bis-diglyceryl polyacyladipate-2 | 4.00% |
| Ceresin | 24.00% |
| Titanium dioxide | 1.00% |
| Carmine red | 1.00% |
| D&C Red No. 7 | 3.00% |
| Polyethylene | 1.00% |
| Silicone methacrylate particles from Ex. 1 | 1.00% |
| Aluminium starch octenylsuccinate & lauroyllysine | 1.00% |

Example 14: Mascara Formulation According to Table 12

TABLE 12

| Formulation according to Example 14 | |
|---|---|
| Sucrose stearate | 4.00% |
| Polyglyceryl-3 methylglucose distearate | 2.00% |
| Stearyl alcohol | 1.00% |
| Candelilla wax | 5.00% |
| Carnauba wax | 1.75% |
| Beeswax | 4.25% |
| Hydrogenated rice bran wax | 5.00% |
| Adipic acid/diethylene glycol/glycerol crosspolymer | 5.00% |
| Ceramide NP | 0.05% |
| Iron oxide | 10.00% |
| Silicone methacrylate particles from Ex. 1 | 0.50% |
| Water | to 100% |
| 1,3-Butanediol | 3.00% |
| Triethanolamine | 1.80% |
| Acrylate/octylacrylamide copolymer | 5.00% |
| Phenoxyethanol; methylparaben; ethylparaben; butylparaben; propylparaben, isobutylparaben | 0.60% |
| Phenoxyethanol | 0.50% |

Example 15: Make-Up Foundation According to Table 13

TABLE 13

| Formulation according to Example 15 | |
|---|---|
| Bis(Glyceryl/Lauryl) Glyceryl/Lauryl Dimethicone* | 4.00% |
| Diethylhexyl carbonate** | 3.10% |
| Phenoxyethyl caprylate*** | 3.10% |
| Mineral oil | 6.30% |
| Titanium dioxide | 4.00% |
| Iron oxide | 2.50% |
| Talc | 1.00% |
| Boron nitride | 1.00% |
| Dicaprylyl carbonate (and) stearalkonium hectorite (and) propylene carbonate | 2.00% |
| Silicon methacrylate particles from Ex. 1 | 1.00% |
| Nylon-10/10**** | 1.00% |
| Dimethicone; Dimethicone/Vinyl Dimethicone Crosspolymer | 4.00% |
| Glycerol | 4.00% |
| Magnesium sulphate heptahydrate | 1.50% |
| Water | to 100% |
| Methylparaben; Ethylparaben; Propylparaben; n-Propylparaben; Phenoxtol | 0.70% |

*ABIL ® EM 120 (Evonik Industries AG)
**TEGOSOFT ® DEC (Evonik Industries AG)
***TEGOSOFT ® XC (Evonik Industries AG)
****TEGOLON ® ECO 10-10 (Evonik Industries AG)

Example 16: Blemish Balm with SPF 15 Formulation According to Table 14

TABLE 14

| Blemish balm with SPF 15 formulation according to Example 16 | |
|---|---|
| Polyglyceryl-3 methylglucose distearate* | 3.00% |
| Glyceryl Stearate | 2.50% |
| Stearyl Alcohol | 1.50% |
| Diethylhexyl Carbonate** | 6.90% |
| Aqua; Ethylhexyl Stearate; Sodium Hyaluronate Crosspolymer; Polyglyceryl-4 Diisostearate/Polyhydroxystearate/Sebacate; Sodium Isostearate*** | 2.00% |
| Phytosphingosine | 0.10% |
| Ethylhexyl methoxycinnamate | 5.00% |
| Diethylamino Hydroxybenzoyl Hexyl Benzoate | 3.00% |
| Titanium Dioxide CI 77891 | 3.00% |
| Talc | 2.00% |
| Yellow iron oxide**** | 0.36% |
| Red iron oxide***** | 0.12% |
| Black iron oxide****** | 0.08% |
| Isoamyl cocoate******* | 4.44% |
| Phenoxyethyl caprylate******** | 4.00% |
| Nylon-10/10********* | 1.50% |
| Silicone methacrylate particles from Ex. 1 | 1.50% |
| Water | to 100% |
| Glycerol | 3.00% |
| Hydrolyzed Hyaluronic Acid********** | 0.10% |
| Tetrapeptide-21; Glycerol; Butylene Glycol; Aqua*********** | 2.00% |
| Ethanol | 3.00% |

TABLE 14-continued

Blemish balm with SPF 15 formulation according to Example 16

| | |
|---|---|
| Methylparaben, Ethylparaben, Methylisothiazolinone | 0.80% |

*TEGO ® Care 450 (Evonik Industries AG)
**TEGOSOFT ® DEC (Evonik Industries AG)
***HyaCare ® Filler CL (Evonik Industries AG)
****Unipure Yellow LC 182 (Sensient)
*****Unipure Red LC 381 (Sensient)
******Unipure Black LC 989 (Sensient)
*******TEGOSOFT ® AC (Evonik Industries AG)
********TEGOSOFT ® XC (Evonik Industries AG)
*********TEGOLON ® EC 10-10 (Evonik Industries AG)
**********HyaCare ® 50 (Evonik Industries AG)
***********TEGO ® Pep 4-17 (Evonik Industries AG)

Example 17: Shower Gel Formulation According to Table 15

TABLE 15

Formulation according to Example 17

| | |
|---|---|
| Acrylates/C10-30 Alkyl Acrylate Crosspolymer* | 1.60% |
| Water | to 100% |
| Sodium lauryl sulphate | 21.40% |
| Cocamidopropylbetaine** | 5.30% |
| Polyglyceryl-3 Caprate*** | 0.50% |
| Silicone methacrylate particles from Ex. 1 | 2.00% |
| Sodium hydroxide (10% in water) | q.s. |
| Phenoxyethanol; Methylisothiazolinone | q.s. |
| Perfume | q.s. |

*TEGO ® Carbomer 341 ER (Evonik Industries AG)
**TEGO ® Betain F 50 (Evonik Industries AG)
***TEGOSOFT ® PC 31 (Evonik Industries AG)

Example 18: Conditioner Formulation According to Table 16

TABLE 16

Formulation according to Example 18

| | |
|---|---|
| Water | to 100% |
| Cetrimonium chloride* | 2.00% |
| Behentrimonium chloride** | 2.00% |
| Cyclopentasiloxane; Dimethiconol*** | 1.00% |
| Silicone methacrylate particles from Ex. 1 | 0.50% |
| Cetearyl alcohol**** | 5.00% |
| Phenoxyethanol; methylisothiazolinone | q.s. |
| Perfume | q.s. |

*VARISOFT ® 300 (Evonik Industries AG)
**VARISOFT ® BT 85 (Evonik Industries AG)
***ABIL ® OSW 5 (Evonik Industries AG)
****TEGO ® Alkanol 1618 (Evonik Industries AG)

Example 19: 2-in-1-Shampoo Formulation According to Table 17

TABLE 17

Formulation according to Example 19

| | |
|---|---|
| Sodium lauryl sulphate | 60.00% |
| Sodium cumene sulphonate | 3.00% |
| Water | to 100% |
| Cocamidopropylbetaine* | 8.00% |
| Cocamide MEA** | 1.50% |

TABLE 17-continued

Formulation according to Example 19

| | |
|---|---|
| Glycol distearate*** | 1.50% |
| Cetyl alcohol**** | 0.50% |
| Dimethicone (1000 mPas) | 1.50% |
| Silicone methacrylate particles from Ex. 1 | 1.00% |
| Nylon-10/10***** | 0.50% |
| Xanthan Gum | 0.75% |
| Phenoxyethanol; methylisothiazolinone | q.s. |
| Perfume | q.s. |

*TEGO ® Betain F 50 (Evonik Industries AG)
**REWOMID ® C 212 (Evonik Industries AG)
***TEGIN ® G 100 (Evonik Industries AG)
****TEGO ® Alkanol 16 (Evonik Industries AG)
*****TEGOLON ® ECO 10-10 (Evonik Industries AG)

Example 20: Styling Wax Formulation According to Table 18

TABLE 18

Formulation according to Example 20

| | |
|---|---|
| Water | to 100% |
| Propylene glycol | 2.00% |
| Glycerol | 11.00% |
| Methoxy PEG/PPG-7/3 Aminopropyldimethicone* | 0.50% |
| Isosteareth-20** | 14.50% |
| Laureth-4*** | 10.00% |
| Paraffinum Perliquidum | 6.00% |
| C12-15 Alkyl Benzoate**** | 6.00% |
| Silicone methacrylate particles from Ex. 1 | 1.00% |
| Phenoxyethanol; methylisothiazolinone | q.s. |
| Perfume | q.s. |

*ABIL ® Soft AF 100 (Evonik Industries AG)
**REWODERM ® 66 E 20 (Evonik Industries AG)
***TEGO ® Alkanol 4 (Evonik Industries AG)
****TEGOSOFT ® TN (Evonik Industries AG)

Example 21: Leave-in-Conditioner Formulation According to Table 19

TABLE 19

Formulation according to Example 21

| | |
|---|---|
| Ceteareth-25* | 4.00% |
| Cyclopentasiloxane; Dimethiconol** | 16.00% |
| Methoxy PEG/PPG-7/3 Aminopropyldimethicone*** | 1.00% |
| Silicone methacrylate particles from Ex. 1 | 3.00% |
| Laureth-4**** | 0.50% |
| Carbomer***** | 0.50% |
| Water | to 100% |
| Propylene glycol | 5.00% |
| Sodium hydroxide (10% in water) | to pH 5-6 |
| Perfume | q.s. |
| Phenoxyethanol; methylisothiazolinone | q.s. |

*TEGIN ® ACID C (Evonik Industries AG)
**ABIL ® OSW 5 (Evonik Industries AG)
***ABIL ® Soft AF 100 (Evonik Industries AG)
****TEGO ® Alkanol L 4 (Evonik Industries AG)
*****TEGO ® Carbomer 140 (Evonik Industries AG)

Example 22: Light W/O Cream According to Table 20

TABLE 20

| Formulation according to Example 22 | |
| --- | --- |
| Bis-PEG/PPG-14/14 Dimethicone; Caprylic/Capric Triglyceride* | 3.00% |
| Hydrogenated Castor Oil | 0.80% |
| Microcrystalline Wax | 1.20% |
| Isopropyl Palmitate** | 4.30% |
| Isohexadecane | 4.30% |
| Dimethicone (5 mPas) | 10.40% |
| Silicone methacrylate particles from Ex. 1 | 2.00% |
| Glycerol | 3.00% |
| Sodium Chloride | 2.00% |
| Creatine*** | 0.50% |
| Water | to 100.00% |
| Phenoxyethanol; ethylhexylglycerol | 0.70% |
| Perfume | q.s. |

*ABIL ® EM 97 S (Evonik Industries AG)
**TEGOSOFT ® P (Evonik Industries AG)
***TEGO ® Cosmo C100 (Evonik Industries AG)

Example 23: W/O Moisturizing Cream According to Table 21

TABLE 21

| Formulation according to Example 23 | |
| --- | --- |
| Cetyl PEG/PPG/10/1 Dimethicone* | 2.00% |
| Mineral oil (30 mPas) | 17.00% |
| Hydrogenated Castor Oil | 0.40% |
| Silicone methacrylate particles from Ex. 1 | 2.00% |
| Microcrystalline wax | 0.60% |
| Sodium Chloride | 0.50% |
| Water | to 100.00% |
| Urea | 10.00% |
| Phenoxyethanol; ethylhexylglycerol | 0.70% |
| Perfume | q.s. |

*ABIL EM 90 (Evonik Industries AG)

Example 24: Cationic O/W Formulation According to Table 22

TABLE 22

| Formulation according to Example 24 | |
| --- | --- |
| Distearyldimonium chloride* | 1.00% |
| Polyglyceryl-3 Methylglucose Distearate** | 2.00% |
| Glyceryl Stearate*** | 2.00% |
| Stearyl Alcohol**** | 1.00% |
| Cetyl Ethylhexanoate***** | 9.00% |
| Caprylic/Capric Triglyceride****** | 10.00% |
| Silicone methacrylate particles from Ex. 1 | 1.50% |
| Glycerol | 3.00% |
| Water | to 100.00% |
| Methylparaben, Ethylparaben, Methylisothiazolinone | 0.80% |
| Perfume | q.s. |

*VARISOFT ® TA 100 (Evonik Industries AG)
**TEGO ® Care 450 (Evonik Industries AG)
***TEGIN ® M Pellets (Evonik Industries AG)
****TEGO ® Alkanol 18 (Evonik Industries AG)
*****TEGOSOFT ® CO (Evonik Industries AG)
******TEGOSOFT ® CT (Evonik Industries AG)

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

The invention claimed is:

1. A process for producing silicone (meth)acrylate particles, said process comprising:
   a) producing an emulsion of an aqueous phase and an organic phase, wherein the organic phase has at least one radical initiator and at least one siloxane having at least one (meth)acrylate group of formula (I)

—O—C(O)—CR=CH$_2$  (I)

where R=—H or —CH$_3$,
   with the addition of at least one solid-body emulsifier and mixing of the two phases,
   where the organic phase forms an inner phase of the emulsion, and
   b) fully polymerizing the inner phase of the emulsion in the presence of a radical initiator which is more soluble in the organic phase than in the aqueous phase,
   wherein the at least one siloxane has an average molar ratio of groups of formula (I) to Si atoms of less than 0.1;
   wherein the at least one siloxane is a compound of formula (II):

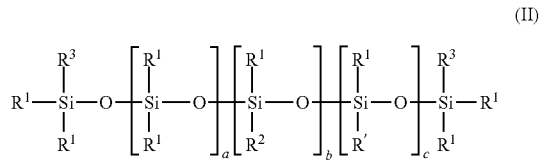

wherein
   R$^1$ is a methyl radical;
   R$^2$ is independently selected, for each occurrence in Formula (II), from radicals having the formula —(CH$_2$)$_3$—O—CH$_2$—CH(OH)—CH$_2$—O—C(O)—CH$_3$;
   R$^3$ is independently selected, for each occurrence in Formula (II), from a methyl radical or radicals that have a group according to formula (I);
   R' is independently selected from groups according to formula (I);
   a=9 to 250;
   b=0 to 20;
   c=0 to 20;
   and with the proviso that, per siloxane of formula (II), if c=0, at least one radical R$^3$ is present which has a group according to formula (I).

2. The process according to claim 1, wherein the radical initiator is added in a concentration of 0.05 to 2% by weight, based on the inner phase of the emulsion.

3. The process according to claim 1, wherein the solid-body emulsifier has an average particle size d$_{50}$ of >100 nm to 200 nm.

4. The process according to claim 1, wherein the solid-body emulsifiers are selected from metal oxides, mixed oxides, nitrides, hydroxides, carbonates and silicates which are at least (partially)hydrophobicized with at least one compound selected from the group consisting of silanes, siloxanes, quaternary ammonium compounds, cationic polymers and fatty acids or anions thereof.

5. The process according to claim 1, wherein the at least siloxane having at least one (meth)acrylate group of formula (I) contains said group in the form of a radical selected from at least one of

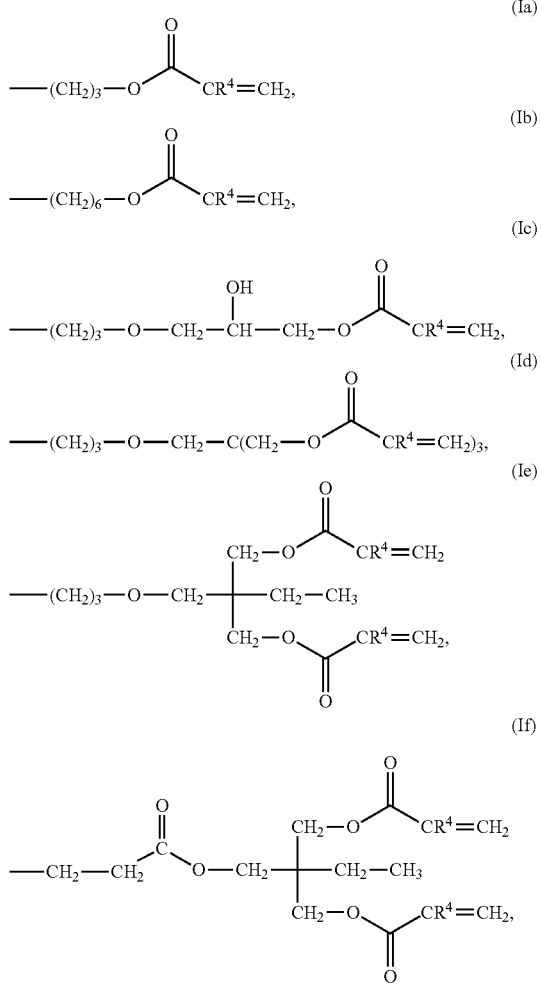

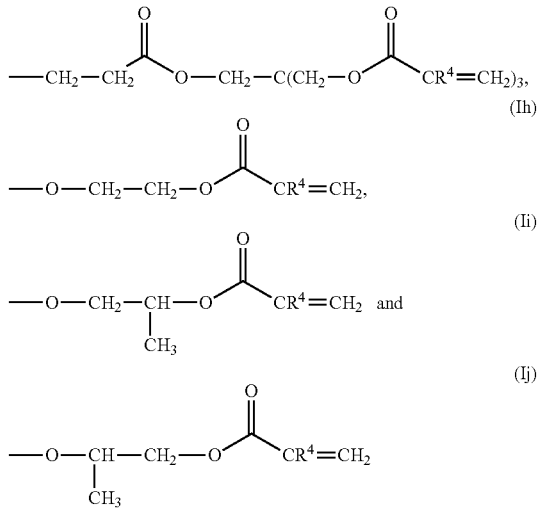

where R⁴ is hydrogen or a methyl group.

6. The process according to claim 5, wherein the radical is selected formulae (Ib) and (Ie).

7. The process according to claim 1, wherein the variable a is from 50 to 220.

8. The process according to claim 1, wherein the variable c is a value from 4 to 12, or c=0 and all of the radicals R³ are those radicals which have a group according to formula (I).

9. The process according to claim 1, wherein the organic phase contains substances which can be released from the silicone (methacrylate) particles, wherein said substances which can be released are selected from cosmetic oils, fragrances, silver and silver-containing compounds, dyes, and preservatives.

10. A composition of matter comprising the particles according to claim 1.

11. The composition of matter according to claim 10, wherein the particles are dispersed in an aqueous or an organic media.

12. The process according to claim 1, wherein the at least one siloxane has an average molar ratio of groups of formula (I) to Si atoms of 0.02 to 0.08.

* * * * *